(12) United States Patent
Chen et al.

(10) Patent No.: US 9,592,362 B2
(45) Date of Patent: Mar. 14, 2017

(54) METHOD OF MAKING ABSORBABLE MICROTUBES AND THE PRODUCT THEREOF

(75) Inventors: Gaoyuan Chen, Hillsborough, NJ (US); James Matrunich, Mountainside, NJ (US)

(73) Assignee: Ethicon, Inc., Somerville, NJ (US)

( * ) Notice: Subject to any disclaimer, the term of this patent is extended or adjusted under 35 U.S.C. 154(b) by 2587 days.

(21) Appl. No.: 11/201,371

(22) Filed: Aug. 10, 2005

(65) Prior Publication Data

US 2007/0035061 A1 Feb. 15, 2007

(51) Int. Cl.
| | |
|---|---|
| B29C 47/90 | (2006.01) |
| A61M 25/00 | (2006.01) |
| A61L 31/14 | (2006.01) |
| B29C 55/22 | (2006.01) |

(52) U.S. Cl.
CPC ....... *A61M 25/0009* (2013.01); *A61L 31/148* (2013.01); *B29C 55/22* (2013.01); *B29K 2995/006* (2013.01)

(58) Field of Classification Search
USPC ... 264/209.5, 211.2, 210.6, 204, 288.4, 29.2, 264/178 R, 211.13; 210/500.23; 425/66
See application file for complete search history.

(56) References Cited

U.S. PATENT DOCUMENTS

| | | | |
|---|---|---|---|
| 3,228,877 A * | 1/1966 | Mahon | 210/638 |
| 3,630,824 A | 12/1971 | Rohlig | |
| 4,175,326 A * | 11/1979 | Goodson | 433/80 |
| 4,720,384 A | 1/1988 | Di Luccio et al. | |
| 5,100,379 A | 3/1992 | Wendell | |
| 5,458,582 A | 10/1995 | Nakao | |
| 5,741,452 A * | 4/1998 | Ryan et al. | 264/209.5 |
| 6,281,262 B1 | 8/2001 | Shikinami | |
| 2007/0215540 A1* | 9/2007 | Tada et al. | |
| 2007/0222104 A1* | 9/2007 | Sukuzi | 264/204 |
| 2008/0015547 A1* | 1/2008 | Beisel | 604/523 |

FOREIGN PATENT DOCUMENTS

| | | |
|---|---|---|
| EP | 0420541 A2 | 4/1991 |
| JP | 07156251 A | 6/1995 |
| WO | WO 02/058912 A | 8/2002 |

OTHER PUBLICATIONS

International Search Report dated Dec. 7, 2006 for corresponding Appln. No. PCT/US2006/029838.

* cited by examiner

*Primary Examiner* — James Sanders
(74) *Attorney, Agent, or Firm* — Roberts Mlotkowski Safran Cole & Calderon, P.C.

(57) ABSTRACT

A method for making an absorbable microtube comprising the steps of a) extruding an absorbable polymer melt through a die to produce a molten extrudate; b) passing the molten extrudate vertically through an air gap ranging from about 0.1 to 0.5 inch as measured-from-the tip of the die to the surface of a liquid quenching medium to produce a quenched extrudate; and c) drawing the quenched extrudate to produce a drawn tube having an outer diameter of about 4 to about 12 mil; and an absorbable microtube that is made according to this method.

11 Claims, 3 Drawing Sheets

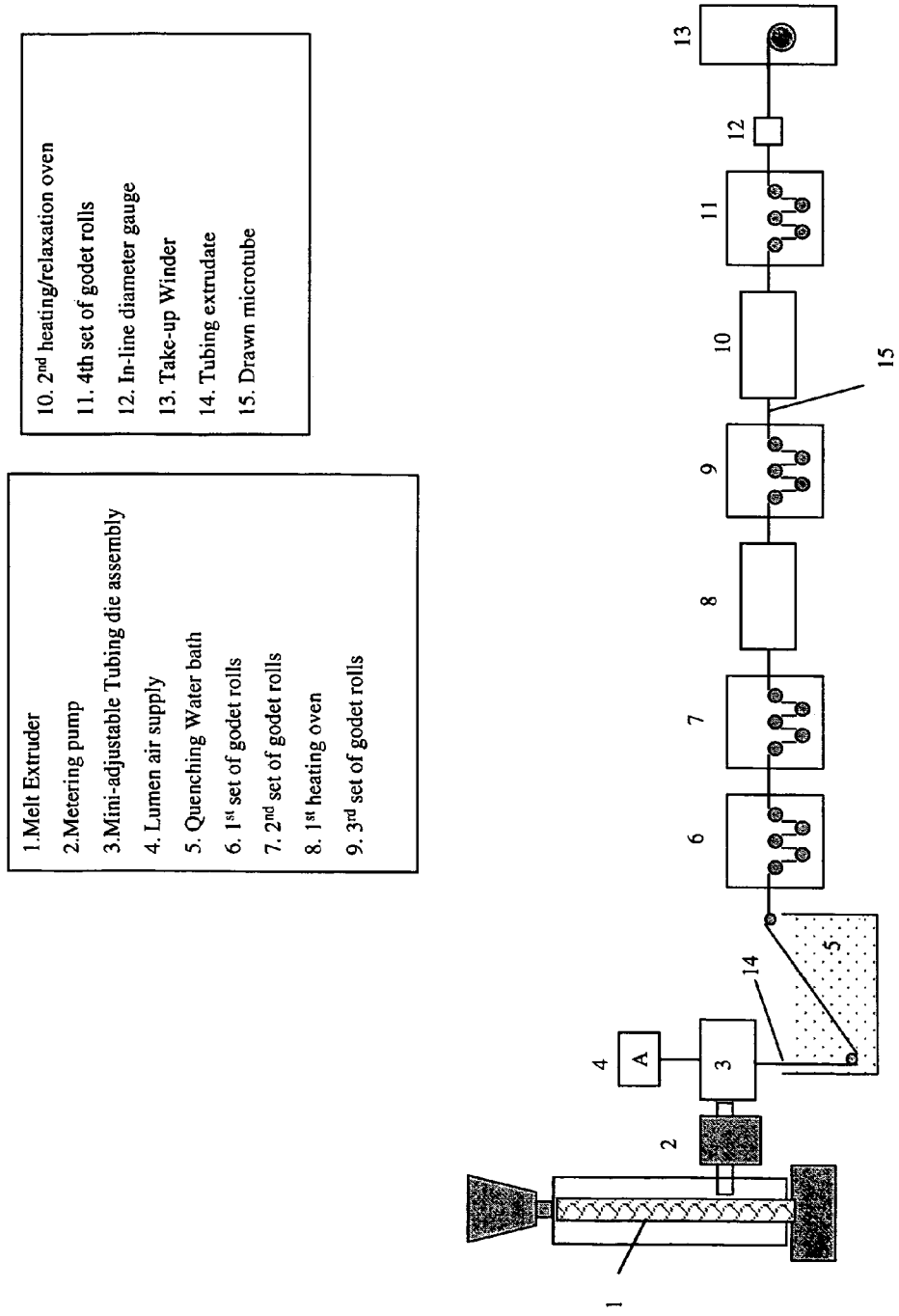
Figure 1. A process
for making the uniform dimensionally stable microtubes

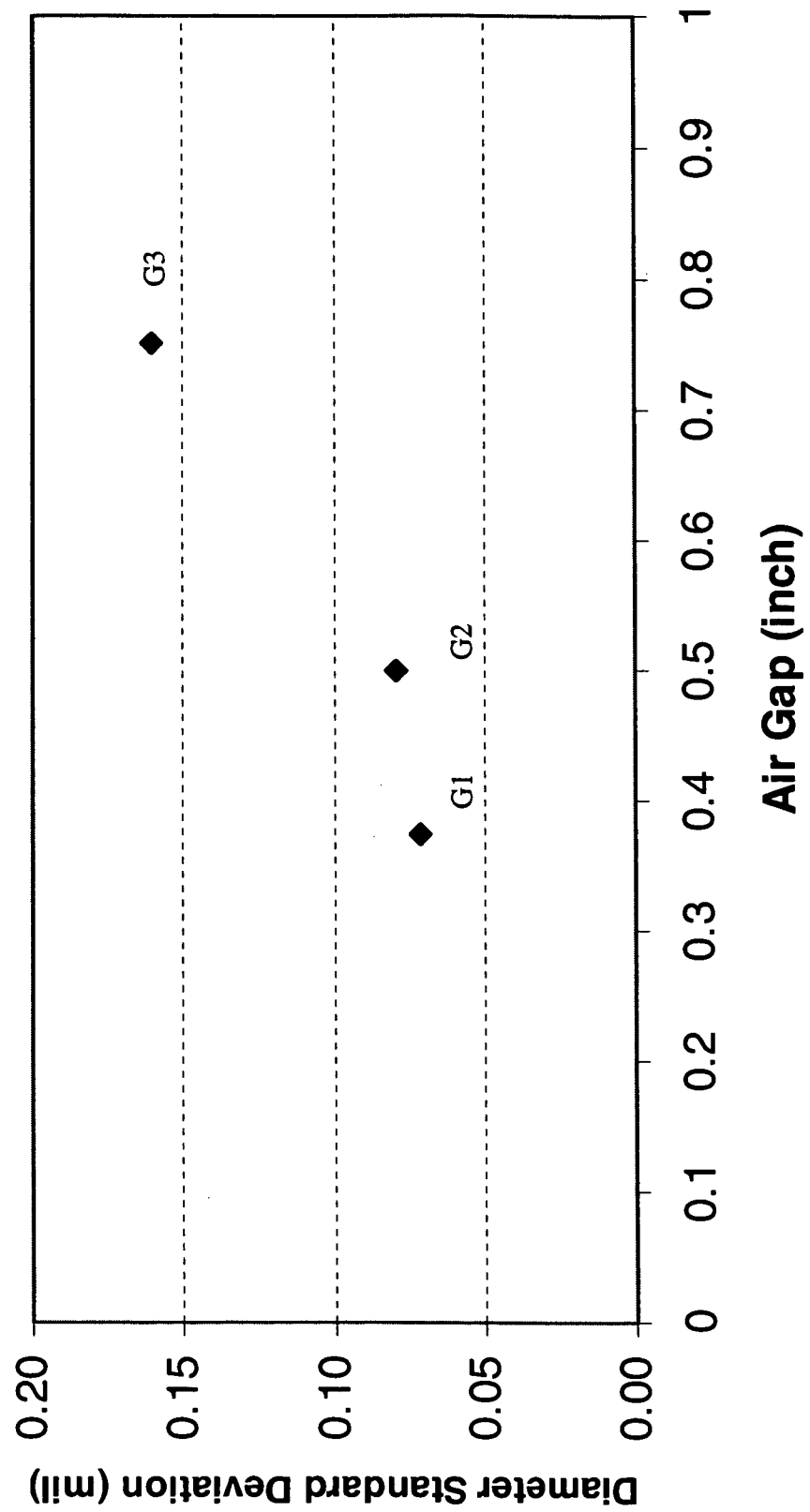
Figure 2. Effect of Air Gap on Microtube Uniformity

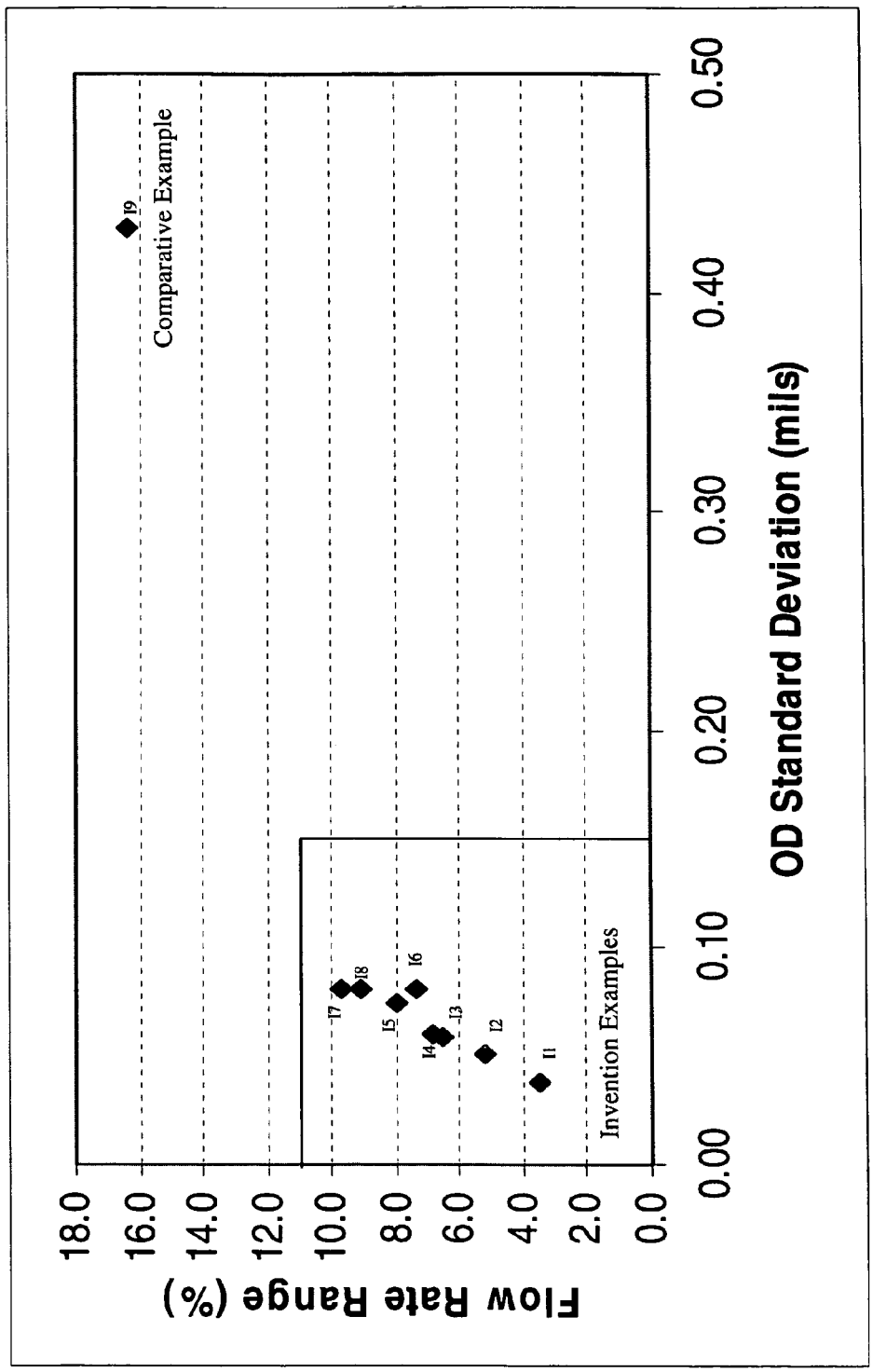
Figure 3. Observed Flow Rate Range as a function of OD standard deviation

METHOD OF MAKING ABSORBABLE MICROTUBES AND THE PRODUCT THEREOF

BACKGROUND OF THE INVENTION

1. Field of the Invention

The present invention relates generally to surgical instruments, and in particular to microtubes, and methods of processing them.

2. Background Discussion

Microtubes are fine tubes having very small outer and inner diameters. As used herein, the term "microtube" refers to a fine tube having an outer diameter ranging from about 4 to about 12 mil (1 mil=1/1000 in or 0.0254 mm).

Microtubes can be used in a number of applications in the medical industry, such as infusion of fluids, drainage of fluids, delivery of anesthesia, and the like. In order to reduce patient discomfort and other complications associated with the removal of the microtubes, it is desirable for such microtubes to be made from absorbable materials so that the microtubes may be left in the body and eventually absorbed within the body. Further, in order to minimize the amount of material that must be absorbed and metabolized by the body, it is desirable that wall thickness of the microtubes be as small as possible. Finally, when such microtubes are utilized for the infusion of fluids or the delivery of anesthesia, controlling the flow rate and delivery of fluids through the microtube for extended periods of time is essential. As a result, microtubes used for these purposes must have uniform inner and outer diameters and cross section throughout the entire length thereof.

However, production of uniform absorbable microtubes has always presented difficulties that are not easily overcome. For example, it is very difficult to produce absorbable microtubes having a variation of outer diameter of 0.15 mil or less, which is required for the control of a uniform flow of a fluid within 15% of a target flow rate. Maintaining dimensional stability of the microtube upon heating, sterilizing, loading, handling or implanting has also been a challenge because of the small diameters and thin walls of the microtube. Additionally, consistent production of a high strength and flexible microtube having such uniformity and dimensional stability is also problematic.

U.S. Pat. No. 4,720,384 teaches a process for preparing a hollow tube drug delivery system, where a polymer solution or suspension of polyolefins, polyurethanes, ethylene-vinyl acetate copolymers, polyvinyl alcohols, or blends of water-soluble polymers with some of the aforementioned polymers, was extruded through an annular orifice to form hollow core. A drug solution was simultaneously extruded into the hollow core to form a drug encapsulated tubular system. The extruded tubular system was coagulated under conditions to minimize orientation and to create pores in the polymeric tube wall. However, since the hollow tube has no molecular orientation and has pores in the wall, such a tubular system would be very weak or brittle and easily kinked or broken upon bending or loading of a force. Further, this reference is silent with respect to a microtube made from absorbable materials and the uniformity of the inner and outer diameters and cross section of the hollow tube.

JP07156251 describes production equipment for making small diameter tubes where the range of fluctuation in the outer diameter, inner diameter, wall thickness of the tubes are held to a minimum. This reference describes the use of a protective member at the output portion of the extruder head in order to prevent the extruded tube from being affected by wind. However, this reference is silent with respect to making of an oriented absorbable microtube with the strength and the dimensional stability thereof.

U.S. Pat. No. 5,100,379 describes a microcatheter having improved tensile strength so as to materially inhibit if not completely preclude the danger of breakage on removal from the body. The microcatheter is prepared by stretching or elongating a tubular article of greater diameter to molecularly orient the tubular walls while reducing the outer diameter to the desired microcatheter size of about 9 mil (or 0.229 mm). Nylons, polyurethanes and polyolefins are described as being suitable polymeric material to be employed to prepare the tubing. However, this reference is silent with respect to a microcatheter made from absorbable materials, and the dimensional stability of the microcatheter upon loading, heating, sterilizing, handling or implanting. While elongating and thereby molecularly orienting a polymeric catheter usually leads to a higher breaking strength, a mechanically oriented and stretched microcatheter has a very high potential to shrink, i.e., has low dimensional stability, upon exposure to heat or a high temperature during sterilization or storage, or after implantation in a human body.

U.S. Pat. No. 3,630,824 teaches a process to make extruded and stretched industrial monofilaments having a outer diameter of about 31.5 to 315 mil, and an inner diameter that is about 0.1 to 15 percent of the outer diameter. These industrial monofilaments are formed from fiber-forming thermoplastic polymers, for example, by spinning or extruding the polymer melt from a spinning head that is mounted in a vertical extrusion position. Such monofilaments are designed to be of a high-loading capacity, which is achievable by reducing the hollow cross section of the monofilament to less than 15 percent of the total cross section of the monofilament, thereby permitting one to achieve nearly the same loading capacity as a completely solid monofilament. This references discloses that the fine longitudinal channel located on the central axis of the monofilament apparently causes uniform shrinkage over the entire length of the monofilament upon cooling of the monofilament after spinning or extrusion. Further, this reference states that a second stage of stretching in a hot air zone develops the tensile strength in the large annular solid portion of the monofilament, while retaining a substantially uniform fine concentric channel which is so reduced in size that the total tensile strength is only slightly reduced from that of a corresponding filament having a completely solid cross section. However, this reference is silent with respect to a microtube made from absorbable materials and the dimensional stability of the hollow monofilament.

Therefore, there remains a need for producing a microtube from absorbable materials with uniform inner and outer diameters and cross section throughout the entire length thereof, superior dimensional stability and high strength, which is capable of controlling flow rate of therapeutic fluid without a rate-controlling device.

SUMMARY OF THE INVENTION

Described herein is a method for making an absorbable microtube comprising the steps of a) extruding an absorbable polymer melt through a die to produce a molten extrudate; b) passing the molten extrudate vertically through an air gap ranging from about 0.1 to 0.5 inch as measured from the tip of the die to the surface of a liquid quenching medium to produce a quenched extrudate; and c) drawing the quenched extrudate to produce a drawn tube having an outer diameter of about 4 to about 12 mil; and a microtube that is made according to this method.

BRIEF DESCRIPTION OF THE DRAWINGS

FIG. 1 depicts a process for making the uniform dimensionally stable microtubes.

FIG. 2 shows the effect of the air gap on the uniformity of the microtube.

FIG. 3 shows the observed flow rate range as a function of OD standard deviation.

DETAILED DESCRIPTION OF THE INVENTION

In order to avoid patient discomfort and other complications associated with the removal of the microtube when delivery of a fluid or anesthesia is accomplished, it is desirable that the microtube be absorbable. It is preferable that the material is essentially absorbed by the body within a period of 2-4 months. Absorbable materials that may be utilized to make the microtubes described herein include but are not limited to polydioxanone, copolymers of polyglycolide and polycaprolactone (PGA/PCL), polyglycolide (PGA), copolymers of polyglycolide and polylactide (PGA/PLA), and the like.

Because the microtube can remain in the body until it is fully absorbed, it is desirable to minimize the amount of absorbable material used to make the microtube. Therefore, it is desirable that the microtube has an outside diameter in the range of about 4 to about 12 mil and a wall thickness in the range of about 1 to about 3 mil, since large tubes with thicker walls may cause more tissue reactions and discomfort to the patients. Preferably, the microtube has an inner diameter ranging from about 2 to about 6 mil.

A critical feature of the microtube described herein is the uniformity of the inner diameter of the microtube, which has been found to be critical to controlling the flow rate of fluids through the microtube. For example, in order to achieve a constant flow rate in the range from 0.5-4.0 ml/hr of fluid for a microtube having a length of 30 cm or less, the inner diameter should be in the range of about 3-5 mil. However, since it is difficult to readily measure the inner diameter of the microtube during processing, the outer diameter of the microtube may be controlled instead and continuously measured in-line, preferably after the in-line annealing. In this case, it is desirable that the standard deviation of the outer diameter be less than about 0.15 mil, more preferably less than about 0.13 mil, in order to obtain a controlled flow rate with a variation of no more than 15%.

Another critical feature of the microtube described herein is that it must have "dimensional stability", which is defined as the resistance to change in physical dimensions upon heating or stretching under a force. One or a combination of the following parameters may be used to evaluate the dimensional stability of a microtube: i) thermal shrinkage upon exposure to a high temperature, e.g., 65° C.; or ii) ultimate elongation, i.e., the elongation at the maximum load.

For example, it has been found that the flow rate of a microtube having a length of 30 cm or less and an inner diameter in the range of about 3 to 5 mil, may change by more than 15% after a vacuum drying process and sterilization, if the length of the microtube shrinks 4% or more during such processing steps or when subjected to heat after processing. Therefore, it is clearly desirable that the microtube does not shrink or change its dimensions when exposed to an elevated temperature during various manufacturing processes and/or during storage, in order to minimize polymer degradation or product property changes. It is preferable that the thermal shrinkage measured at 65° C. (TS %@65° C.) is less than about 3%, more preferably between 0 to about 2% for a microtube having a length of 30 cm or less and an inner diameter in the range of about 3 to 5 mil.

The microtube described herein also exhibits a good resistance to deformation when it is slightly tensioned or stretched, accidentally or intentionally, during the process of assembling, detachment testing, handling, or implanting into tissues, for example, where as much as one pound of force could be applied. Therefore, it is preferable that the ultimate elongation (UE) of the microtube does not exceed about 28%. If the UE of a microtube is greater than about 28%, the product can be easily deformed upon loading of a small force (e.g. one pound) and at least part of that deformation cannot be recovered after the load is removed, potentially resulting in a change in the inner diameter of the microtube and hence the flow rate of a fluid. More preferably, the UE of the microtube is less than about 22%.

The microtube described herein may be made via the process schematically illustrated in FIG. 1. Critical steps of the process described herein to control the uniformity of the inner and outer diameters and the cross section of the microtube are vertically extruding the absorbable polymer melt through an annular orifice at the bottom of the tubing die 3; and passing the molten tubing extrudate 14 through an air gap ranging from about 0.1 to 0.5 inch as measured from die tip to the surface of the liquid quenching medium.

Generally, the process also includes the steps of drawing the tubing 14 continuously in one or multiple steps with one or more sets of drawing rolls 7 and 9, so the drawn tube has an outer diameter of about 4 to about 12 mil and a drawn ultimate elongation of about 28% or less; and annealing the drawn tubing 15 at a temperature of at least about 50° C., more preferably in the range of about 60° C. to about 150° C., so that the thermal shrinkage is less than about 3%.

Annealing is conducted on the oriented microtube to impart dimensional stability to the microtube. The annealing may be done in an in-line fashion with a non-contact heating oven 10, at a temperature of about 50° C. to 150° C. and an oven length of two feet or longer or for a total time of about 2 seconds or longer, as shown in FIG. 1, and/or in an off-line fashion in a heated oven (not shown) for several hours. During in-line annealing, the orientated microtube length may be kept constant or allowed to relax up to about 12%, for example, as calculated by the percent change of the speed of the relax roll 11 compared to the speed of the preceding draw roll 9.

Off-line annealing may be conducted on the microtubes in a heated oven at a temperature of about 50° C. to 150° C., under nitrogen or vacuum for about 2 to 32 hours to remove residual monomers and/or additional internal stress that may still remain in the microtubes to assure good dimensional stability. When the off-line annealing is carried out, the length of the microtube may be kept constant or allowed to change up to about 5%. If the length of microtube is allowed to relax more than about 5% during the off-line annealing process, the inner diameter and the UE of the microtube may change substantially, which could result in undesirable changes in flow rate. More preferably, the length of the microtube may be allowed to change up to about 3%.

It is preferable to allow the oriented microtube to retract or relax by about 2% to about 12% while it is being heated to a high temperature continuously in-line where the tubing is being extruded and formed. This way, the final lumen size can be readily controlled by adjusting the lumen air pressure, polymer throughput, and/or the take-up speed of the drawn and relaxed microtube. However, off-line annealing, with or without relaxation, may be conducted as necessary to achieve the low level thermal shrinkage property described herein.

Test Methods

Diameter Test

The outside diameter (OD) of the microtubes can be measured with a non-contact diameter gauge such as LASERMIKE model 2021 Dual SPC Processor and 200-025 Dual Axis Scanner. The measurement is preferably done in-line while the microtube is being produced, i.e., after in-line annealing. The running microtube can be scanned every half a second. Average OD and OD standard deviation (OD-s) can be calculated by the SPC processor based on a sample size of 20 scans, and a subgroup size of 20 samples. A statistical report can be printed out every 3 minutes and 20 seconds. The average OD and OD-s over a period of 15 minutes or more may be obtained under a given set of processing conditions.

Flow Rate Uniformity Test

Flow rate and flow rate uniformity through a microtube may be tested with a flow meter such as a gas flow meter, model #M-5SCCM-D, supplied by Alicat Scientific Inc. The microtube may be cut into a convenient length such as 10-30 cm (or 4.0-12 in). Test pressure may be in the range of 2-8 psi. For a given size or lot of microtube samples, the tube length and test pressure should be fixed in order to determine the average and variation range of the flow rate. Nitrogen gas or ambient air may be used for the flow rate test. About 10 or more tube samples should be tested for calculating the average and variation range of the flow rate.

Thermal Shrinkage Test

Thermal shrinkage can be tested with a shrinkage tester, for example MK V, manufactured by TESTRITE LTD. Shrinkage of microtubes can be tested by following the same procedure for yarns, cords, etc., described in the User's Manual (Directions for use) provided by TESTRITE LTD. More specifically, the following testing parameters can be used for testing the microtube samples: operating temperature of 65° C.; testing time of 2 minutes; clip weight of 9 grams. To minimize the effect of clip weight, two or more of microtube samples may be aligned together in parallel and attached to the standard clip weight of 9 grams. The average shrinkage of the two or more microtube samples can be thus recorded. The test can be repeated once or twice if the deviation between any two tests is significant and an average of all the tests on the same type of specimen can be reported.

Tensile Test

Tensile properties of microtubes can be obtained with an Instron universal testing instrument such as model #4201, #4301, or #4464. The test can be performed with a gauge length of 5 inches, a cross-head speed of 12 in/min. Cord and yarn type clamps or flat clamps with steel face grips can be used in testing the microtubes, provided that there are no severe clamp breaks or slippage (clamps with rubber faced grips are not recommended due to the fact that test results could be different as a result of possible jaw penetration or slippage). Air pressure of 40 psi is preferred for the pneumatic clamps, which may be adjusted, if necessary, to minimize clamp breaks or slippage. The tensile data can be obtained directly with Instron Series IX Automated Materials Tester Program such as version 7.51.00

EXAMPLES

Examples Showing the Effect of Air Gap on Microtube Uniformity Made from 90/10 PGA/PLA Examples G1-G4 were produced under the processing conditions given in Table 1. This experiment demonstrates the effect of the distance from die exit to the quench water surface (i.e., air gap) on uniformity of the outer diameter. Examples G1, G2 and G3 were produced with an air gap of 0.5" or less, which resulted in an OD standard deviation of less than 0.10 mils, as shown in FIG. 2, while Example G4, which was produced with an air gap of 0.75 inches, resulted in an OD standard deviation exceeding 0.15 mils. The outer diameter was measured after in-line annealing.

TABLE 1

Effect of Air Gap on Diameter Uniformity of Microtubes Produced from 90/10 PGA/PLA copolymer

| | Example Number | | | |
|---|---|---|---|---|
| | G1 | G2 | G3 | G4 |
| Die Temp. (° C.) | 218.3 | 218.3 | 218.3 | 218.3 |
| Tubing Die ID (mil) | 70 | 70 | 70 | 70 |
| Tip OD (mil) | 30 | 30 | 30 | 30 |
| Lumen Air Pressure (inch H$_2$O) | 13.0 | 13.0 | 14.0 | 12.0 |
| Throughput (g/h) | 41.0 | 41.0 | 41.0 | 41.0 |
| Jet Velocity (ft/min) | 0.8 | 0.8 | 0.8 | 0.8 |
| Air Gap (inch) | 0.38 | 0.38 | 0.50 | 0.75 |
| Quench Water Tamp (° C.) | 22.0 | 22.0 | 22.0 | 22.0 |
| Godet Roll 1 Speed (FPM) | 10.2 | 10.2 | 10.2 | 10.2 |
| Total Draw Ratio | 5.5 | 5.5 | 5.5 | 5.5 |
| In-Line Annealing Temp. (° C.) | 88.0 | 88.0 | 88.0 | 88.0 |
| In-line Relax % | 0 | 0 | 0 | 0 |
| Drawn Ultimate Elongation (DUE %) | 24.4 | 24.4 | 22.5 | not tested |
| Average OD (mils) | 7.85 | 7.85 | 7.92 | 7.96 |
| OD Standard Deviation (mil) | 0.080 | 0.080 | 0.090 | 0.160 |
| Calculated Wall (mil) | 2.43 | 2.43 | 2.36 | 2.39 |
| Calculated ID (mil) | 3 | 3 | 3.2 | 3.19 |

This experiment demonstrates that it is critical to keep the air gap at less than 0.75 inch, more preferably within the range of about 0.1 to 0.5 inch from tubing die surface to the quench water. If the air gap is less than about 0.1 inch, the quench water may contact the tubing die and freeze the molten polymer jet in the die. If the gap is 0.75 inch or higher, the uniformity of the outer diameter deteriorates, as evidenced by the increase of OD standard deviation. Microtubes having high standard deviation in diameter yield less uniform fluid flow as shown below.

Examples Showing the Effect of Outer Diameter Standard Deviation on Flow Rate

Examples I1-I8 were produced under process conditions similar to those described for Example E1. The samples had a standard deviation in outer diameter in the range of 0.04-0.08 mil (as measured after in-line annealing). Example I9 was produced with less optimized conditions and had an outer diameter standard deviation of 0.43 mil. Nine to ten microtube specimens of each of the above samples were tested with a non-destructive test method (using a air or nitrogen instead of water), which can be directly correlated with a water flow rate. Table 2 contains the data of the test parameters and test results. The observed average percentage flow range was plotted in FIG. 3. In order to control the flow rate range to about 15% or less for a microtube having a length of 30 cm or less and an inner diameter in the range of about 3 to 5 mil, it is preferable to have an outer diameter standard deviation of less than 0.15 mil.

Example B2 was produced under similar conditions as invention example A1, except it was relaxed 20% during off-line annealing instead of 5% or less. This sample had a UE of about 33%.

TABLE 2

Flow Rate Test Data

| | Sample No. | | | | | | | | |
|---|---|---|---|---|---|---|---|---|---|
| | I1 | I2 | I3 | I4 | I5 | I6 | I7 | I8 | I9 |
| OD-Standard Deviation (mil) | 0.038 | 0.050 | 0.058 | 0.060 | 0.074 | 0.080 | 0.080 | 0.080 | 0.430 |
| ID (mil) | 3.46 | 3.57 | 3.21 | 3.42 | 4.00 | 3.00 | 3.00 | 3.00 | 3.30 |
| Specimen Length (cm) | 15.0 | 15.0 | 25.4 | 15.0 | 23.0 | 15.0 | 15.0 | 15.0 | 17.0 |
| # of Specimens | 10 | 9 | 10 | 10 | 10 | 10 | 10 | 10 | 10 |
| Inlet Pressure of Test Fluid (psi) | 5.20 | 5.20 | 3.80 | 5.20 | 3.80 | 3.80 | 3.80 | 3.80 | 3.80 |
| Test Fluid | N2 | N2 | Air | N2 | N2 | Air | Air | Air | Air |
| Test Fluid Avg Flow of test fluid(ml/h) | 1.41 | 1.64 | 0.54 | 1.52 | 1.07 | 0.86 | 1.06 | 0.87 | 1.22 |
| Test Fluid Flow Rate Standard Deviation | 0.029 | 0.055 | 0.023 | 0.071 | 0.056 | 0.045 | 0.066 | 0.056 | 0.158 |
| Flow Rate Range (%) | 3.50 | 5.24 | 6.50 | 6.87 | 8.02 | 7.33 | 9.70 | 9.10 | 16.40 |

Examples A1 and B1-B2

75/25 PGA/PCL block copolymer melt was made into microtubes using the process shown schematically in FIG. 1. Process conditions and the properties of the microtube samples are given in Table 3.

TABLE 3

Processing Conditions and Properties of 75/25 PGA/PCL microtubes

| | Example Number | | |
|---|---|---|---|
| | A1 | B1 | B2 |
| Die Temp. (° C.) | 200 | 200 | 200 |
| Tubing Die ID (mil) | 100 | 100 | 100 |
| Tip OD (mil) | 30 | 30 | 30 |
| Lumen Air Pressure (inch H2O) | 3.80 | 3.80 | 3.80 |
| Throughput (g/h) | 104.2 | 104.2 | 104.2 |
| Jet Velocity (ft/min) | 0.93 | 0.93 | 0.93 |
| Air Gap (inch) | 5/16 | 5/16 | 5/16 |
| Quench Water Tamp (° C.) | 25.0 | 25.0 | 25.0 |
| Godet Roll 1 Speed (FPM) | 20.7 | 20.7 | 20.7 |
| Total Draw Ratio (TDR) | 8.50 | 8.50 | 8.50 |
| In-Line Annealing Temp. (° C.) | 135 | 135 | 135 |
| In-line Relax % | 10 | 10 | 10 |
| Drawn Ultimate Elongation (DUE %) | 20.0 | 20.0 | 20.0 |
| Average OD (mils) | 8.15 | 8.15 | 8.15 |
| OD Standard Deviation (mil) | 0.055 | 0.055 | 0.055 |
| Calculated Wall (mil) | 2.26 | 2.26 | 2.26 |
| Calculated ID (mil) | 3.62 | 3.62 | 3.62 |
| Off-line Annealing Temp. (° C.) | 105 | None | 105 |
| Annealing Time (hrs) | 6 | None | 6 |
| Off line % Relax | 2 | None | 20 |
| Maximum Strength (lb) | 3.76 | 4.25 | 3.96 |
| Ultimate Elongation (%) | 25.8 | 20.0 | 33.4 |
| Thermal Shrinkage (TS % @ 65° C.) | 0.0 | 8.5 | 0.6 |

The properties of Example A1, especially the dimensional stability parameters of the final product, were in the desirable ranges for a proper control of drug flow rate via a microtube.

Example B1 was produced under similar conditions as invention example A1 but it was not annealed nor relaxed off-line. This sample had shrinkage of about 8.5%.

Examples C1 and D1

Polydioxanone melt was made into microtubes according to the conditions given in Table 4. The properties of the microtube samples are also given in Table 4. Example C1 has satisfactory dimensional stabilities as evidenced by low UE and low shrinkage. Example D1 was made under similar conditions as C1 except that it was not annealed nor relaxed off-line. It has a higher thermal shrinkage of 4.9%.

TABLE 4

Processing conditions and properties of microtubes made from polydioxanone

| | Example Number | |
|---|---|---|
| | C1 | D1 |
| Die Temp. (° C.) | 137.8 | 137.8 |
| Tubing Die ID (mil) | 100.0 | 100.0 |
| Tip OD (mil) | 30.0 | 30.0 |
| Lumen Air Pressure (inch H2O) | 10.0 | 10.0 |
| Throughput (g/h) | 88.5 | 88.5 |
| Jet Velocity (ft/min) | 0.8 | 0.8 |
| Air Gap (inch) | 5/16 | 5/16 |
| Quench Water Tamp (° C.) | 21.0 | 21.0 |
| Godet Roll 1 Speed (FPM) | 24.7 | 24.7 |
| Total Draw Ratio | 6.0 | 6.0 |
| In-Line Annealing Temp. (° C.) | 82 | 82 |
| In-line Relax % | 6 | 6 |
| Drawn Ultimate Elongation (DUE %) | 17.1 | 17.1 |
| Average OD (mils) | 8.1 | 8.1 |
| OD Standard Deviation (mil) | 0.078 | 0.078 |
| Calculated Wall (mil) | 2.25 | 2.25 |
| Calculated ID (mil) | 3.59 | 3.59 |
| Off-line Annealing Temp. (° C.) | 85.0 | None |
| Annealing Time (hrs) | 6 hr | None |
| Off line % Relax | 2.0 | None |
| Maximum Strength (lb) | 2.2 | 1.9 |
| Ultimate Elongation (%) | 22.1 | 17.1 |
| Thermal Shrinkage (TS % @ 65° C.) | 0.0 | 4.9 |

Examples E1-E3 and F1-F2

90/10 PGA/PLA copolymer melt was made into microtubes using similar process as shown in FIG. 1. Processing conditions and the properties of the microtube samples are listed in Table 5.

TABLE 5

Processing Conditions and Properties of Microtubes Produced from 90/10 PGAPLA copolymer

| | Example Number | | | | |
|---|---|---|---|---|---|
| | E1 | E2 | E3 | F1 | F2 |
| Die Temp. (° C.) | 218.3 | 218.3 | 205.6 | 205.6 | 218.3 |
| Tubing Die ID (mil) | 70 | 70 | 70 | 70 | 70 |
| Tip OD (mil) | 30 | 30 | 30 | 30 | 30 |
| Lumen Air Pressure (inch $H_2O$) | 5.6 | 5.6 | 5.0 | 5.2 | 5.8 |
| Throughput (g/h) | 41.1 | 41.1 | 46.8 | 47.2 | 41.3 |
| Jet Velocity (ft/min) | 0.8 | 0.8 | 0.9 | 1.0 | 0.8 |
| Air Gap (inch) | 5/16 | 5/16 | 5/16 | 5/16 | 5/16 |
| Quench Water Tamp (° C.) | 16.0 | 16.0 | 16.0 | 16.0 | 25.0 |
| Godet Roll 1 Speed (FPM) | 8.9 | 9.3 | 9.2 | 8.7 | 11.3 |
| Total Draw Ratio | 7.0 | 7.0 | 7.5 | 7.5 | 5.5 |
| In-Line Annealing Temp. (° C.) | 129.4 | 129.4 | 129.4 | no | 129.4 |
| In-line Relax % | 0 | 5 | 6 | 0 | 0 |
| Drawn Ultimate Elongation (DUE %) | 11.4 | 17.7 | 14.6 | 13.8 | 29.6 |
| Average OD (mils) | 7.99 | 7.99 | 7.99 | 8.00 | 7.95 |
| OD Standard Deviation (mil) | 0.079 | 0.074 | 0.038 | 0.043 | 0.035 |
| Calculated Wall (mil) | 2.00 | 2.00 | 2.26 | 2.29 | 1.98 |
| Calculated ID (mil) | 4.0 | 4.0 | 3.46 | 3.42 | 4.0 |
| Off-line Annealing Temp. (° C.) | 105 | 105 | 105 | None | 105 |
| Annealing Time (hrs) | 6 | 6 | 6 | | 6 |
| Off-line % Relax | 2 | 2 | 2 | | 2 |
| Maximum Strength (lb) | 4.2 | 4.3 | 4.4 | 4.4 | 3.5 |
| Ultimate Elongation (%) | 13.1 | 18.6 | 16.3 | 13.8 | 29.6 |
| Thermal Shrinkage (TS % @ 65° C.) | 0.6 | 0.3 | 0.0 | 9.8 | 0.1 |

Example F1 was produced under similar conditions as example E3 except that the drawn article was neither relaxed in-line nor annealed or relaxed off-line. The sample had a high shrinkage of 9.8%.

Example F2 was produced under similar conditions as example E1 except that the total draw ratio was reduced from 7.0 to 5.5 times. The drawn article had a UE of 29.6%. When this sample was tensioned with one-pound force, it showed a plastic deformation following the yield point. The elongation at 1.0 lb force was 6.4%, significantly greater than the yield point elongation. The differential deformation was 3.2%, which is an indication of plastic deformation.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method for making a microtube comprising the steps of:
   a) extruding an absorbable polymer melt through a die to produce a molten extrudate;
   b) passing the molten extrudate vertically through an air gap having an air gap dimension of about 0.1 to about 0.5 inch, as measured from the tip of the die to the surface of a liquid quenching medium, to produce a quenched extrudate; and
   c) drawing the quenched extrudate to produce a drawn tube having an outer diameter of about 4 to about 12 mil, with an outer diameter standard deviation of less than 0.15 mil and an inner diameter in the range of about 3 to about 5 mil;
   d) controlling the outer diameter standard deviation, and thereby inner diameter uniformity, by maintaining the air gap dimension
   e) annealing the drawn tube in-line at a temperature of about 50° C. to about 150° C.; and
   f) further annealing the drawn tube off-line at a temperature of about 50° C. to about 150° C., to produce said microtube having a dimensional stability as measured by thermal shrinkage at 65° C. of less than 3%.

2. The method for making a microtube according to claim 1, where the steps of annealing are conducted at a temperature of about 60° C. to about 150° C. to produce said microtube.

3. The method for making a microtube according to claim 1, where the quenched extrudate is drawn to an outer diameter of about 6 to about 10 mil.

4. The method for making a microtube according to claim 1, where the quenched extrudate is drawn to an outer diameter of about 7 to about 9 mil.

5. The method for making a microtube according to claim 1, where the air gap ranges from about 0.3 to 0.5 inch.

6. The method for making a microtube according to claim 1, where the step of in-line annealing is conducted for at least about 2 seconds.

7. The method for making a microtube according to claim 1, where the step of off-line annealing is conducted for about 2 to about 32 hours.

8. The method for making a microtube according to claim 1, where the drawn tube is relaxed during in-line annealing up to about 12%.

9. The method for making a microtube according to claim 1, where the drawn tube is relaxed during off-line annealing up to about 5%.

10. The method for making a microtube according to claim 8, where the drawn tube is relaxed during in-line annealing between about 2% to about 12%.

11. The method for making a microtube according to claim 1, where the drawn tube is relaxed during off-line annealing up to about 3%.

* * * * *